(12) United States Patent
Kaufman et al.

(10) Patent No.: US 8,784,459 B2
(45) Date of Patent: Jul. 22, 2014

(54) SPINAL PLATE AND LOCKING SCREW DEVICES, METHODS, AND SYSTEMS

(75) Inventors: Josh Kaufman, Austin, TX (US); Scott Bryant, Austin, TX (US); Greg Calbert, Lakeway, TX (US); John Stokes, Austin, TX (US); Matthew Geck, Austin, TX (US); Landon Gilkey, Austin, TX (US)

(73) Assignee: Genesys Spine, Austin, TX (US)

( * ) Notice: Subject to any disclaimer, the term of this patent is extended or adjusted under 35 U.S.C. 154(b) by 98 days.

(21) Appl. No.: 13/351,340

(22) Filed: Jan. 17, 2012

(65) Prior Publication Data

US 2013/0184767 A1 Jul. 18, 2013

(51) Int. Cl.
  *A61B 17/58* (2006.01)
  *A61B 17/80* (2006.01)

(52) U.S. Cl.
  USPC .......................................... 606/289; 606/286

(58) Field of Classification Search
  USPC ............................ 606/280–281, 286, 289–296
  See application file for complete search history.

(56) References Cited

U.S. PATENT DOCUMENTS

| | | | |
|---|---|---|---|
| 5,549,612 A | 8/1996 | Yapp et al. | |
| 6,152,927 A | 11/2000 | Farris et al. | |
| 6,258,089 B1 | 7/2001 | Campbell et al. | |
| 6,361,537 B1 * | 3/2002 | Anderson | 606/86 B |
| 7,182,782 B2 | 2/2007 | Kirschman | |
| 7,641,701 B2 | 1/2010 | Kirschman | |
| 7,655,028 B2 | 2/2010 | Kirschman | |
| 7,740,649 B2 | 6/2010 | Mosca et al. | |
| 8,216,285 B2 * | 7/2012 | Markworth | 606/294 |
| 8,287,550 B2 * | 10/2012 | Campbell et al. | 606/104 |
| 8,454,666 B2 * | 6/2013 | Tornier | 606/289 |
| 2005/0010227 A1 * | 1/2005 | Paul | 606/71 |
| 2006/0161157 A1 | 7/2006 | Mosca et al. | |
| 2006/0195100 A1 | 8/2006 | Kirschmann | |
| 2008/0021470 A1 | 1/2008 | Ross | |
| 2008/0021476 A1 | 1/2008 | Kirschmann | |
| 2009/0012571 A1 | 1/2009 | Perrow et al. | |
| 2009/0024170 A1 | 1/2009 | Kirschmann | |
| 2009/0275990 A1 | 11/2009 | Enayati | |
| 2011/0319893 A1 * | 12/2011 | Stanaford et al. | 606/70 |

FOREIGN PATENT DOCUMENTS

EP  1 684 673  7/2010

OTHER PUBLICATIONS

Pioneer Surgical, "PAC Plate," 2010, 2 pages.
X-Spine Systems, Inc., "Spider Cervical Plating System," 2010, 2 pages.
Roham Moftakhar, M.D., et al., "Anterior cervical plates: a historical perspective," Jan. 2004, 5 pages.

* cited by examiner

*Primary Examiner* — Nicholas Woodall
*Assistant Examiner* — Larry E Waggle, Jr.
(74) *Attorney, Agent, or Firm* — Trop, Pruner & Hu, P.C.

(57) ABSTRACT

An embodiment of the invention provides for a system, such as a cervical plate fusion system, that has mechanisms for preventing bone screws from backing out of the plate. The system prevents both counter-rotation of the screw and axial backing out of the screw. Other embodiments are described herein.

20 Claims, 6 Drawing Sheets

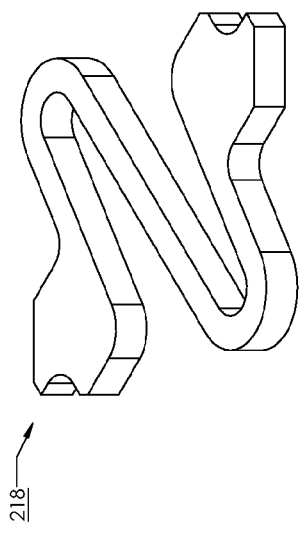
FIG. 2A
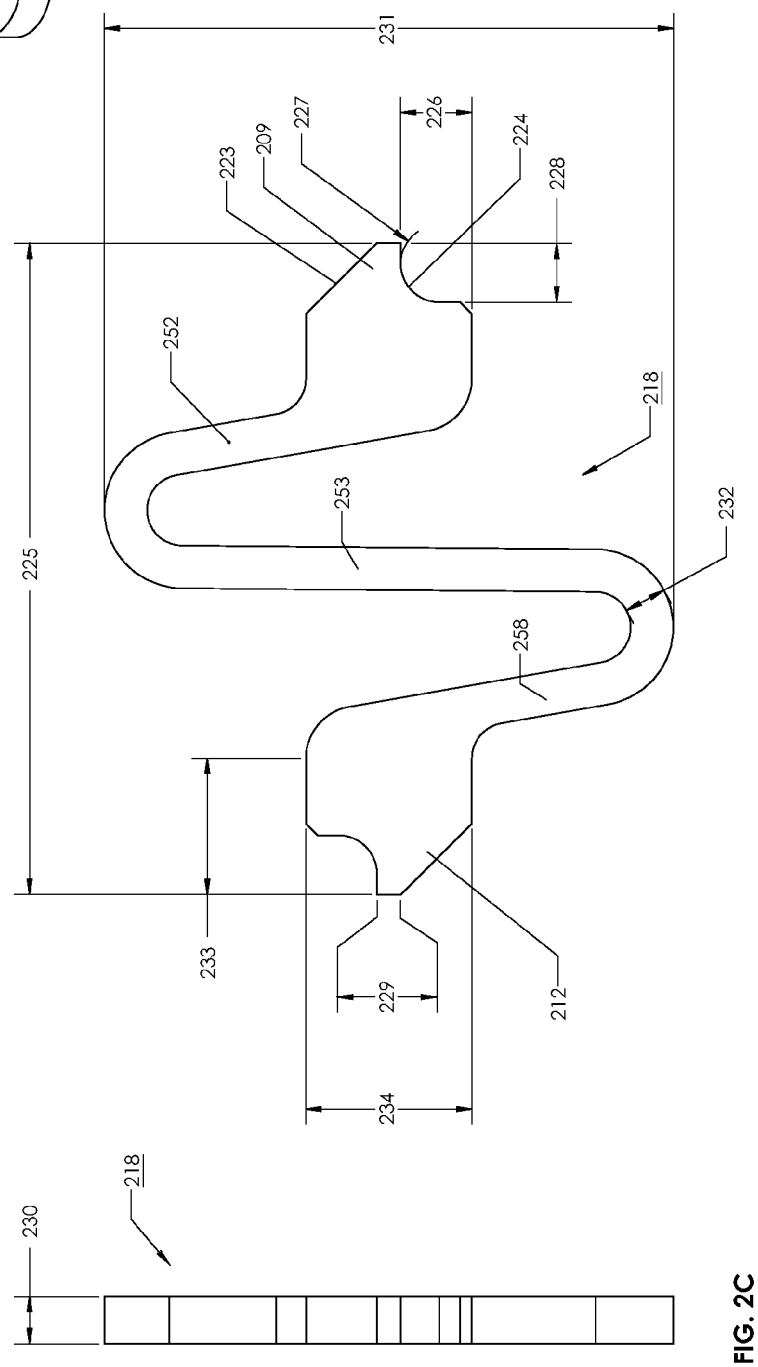
FIG. 2B
FIG. 2C

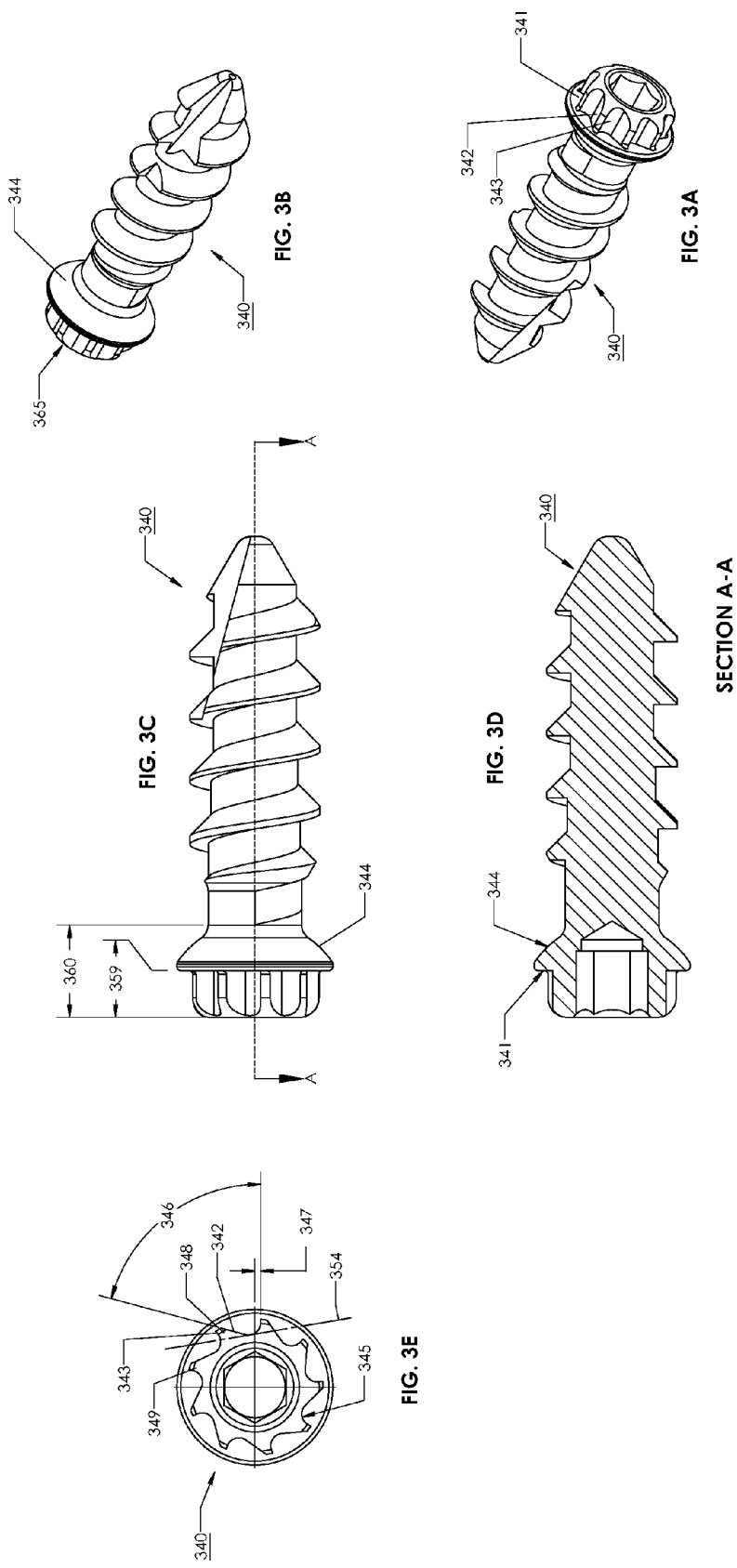

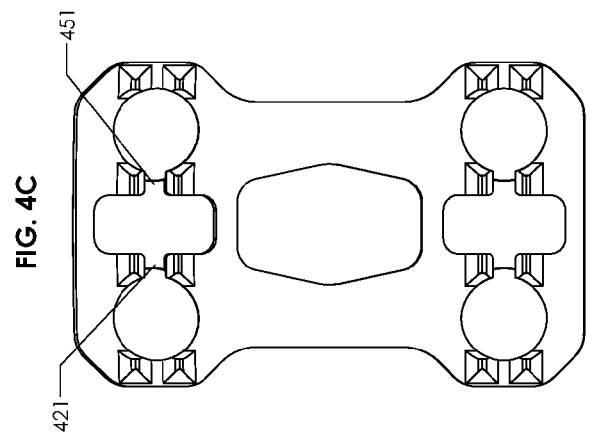
FIG. 4C
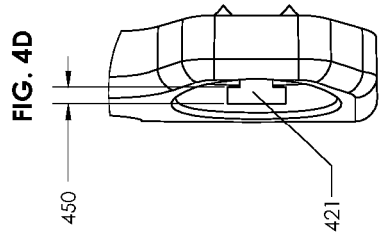
FIG. 4D
FIG. 4B
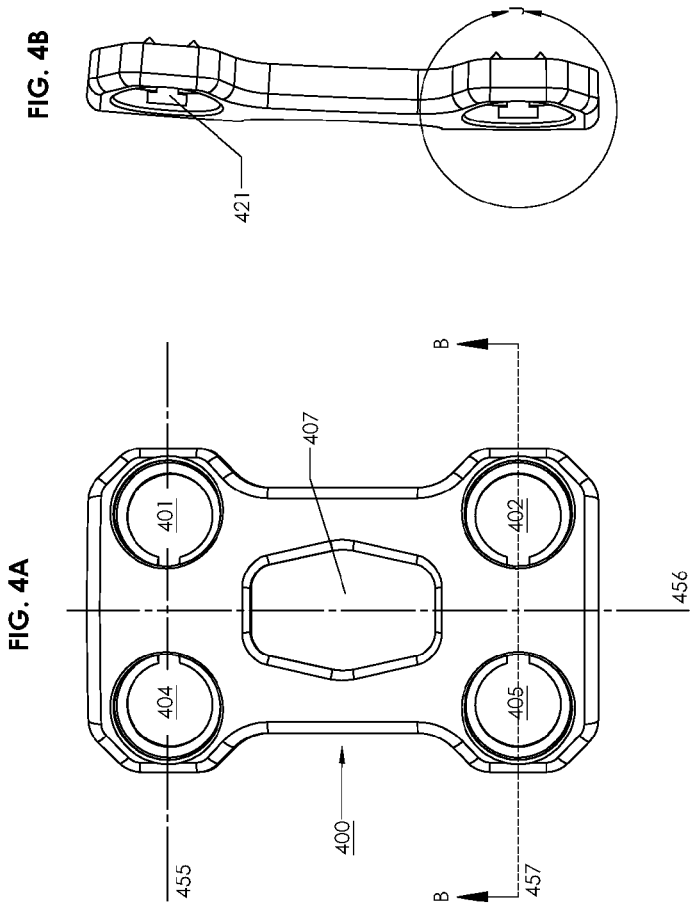
FIG. 4A
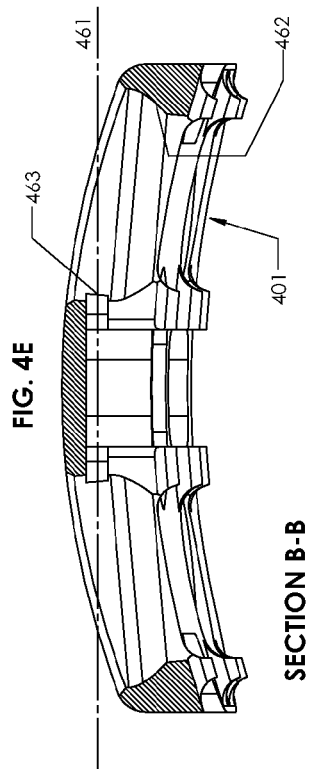
FIG. 4E
SECTION B-B

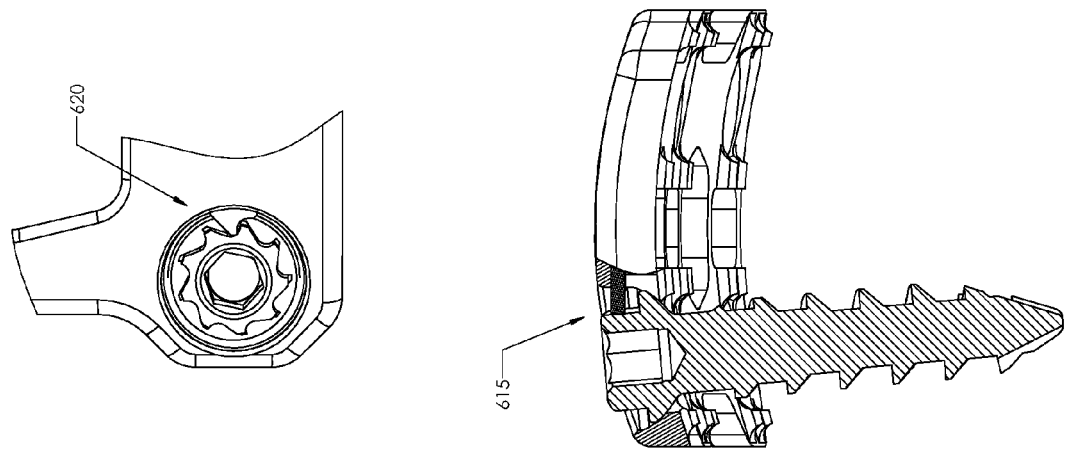
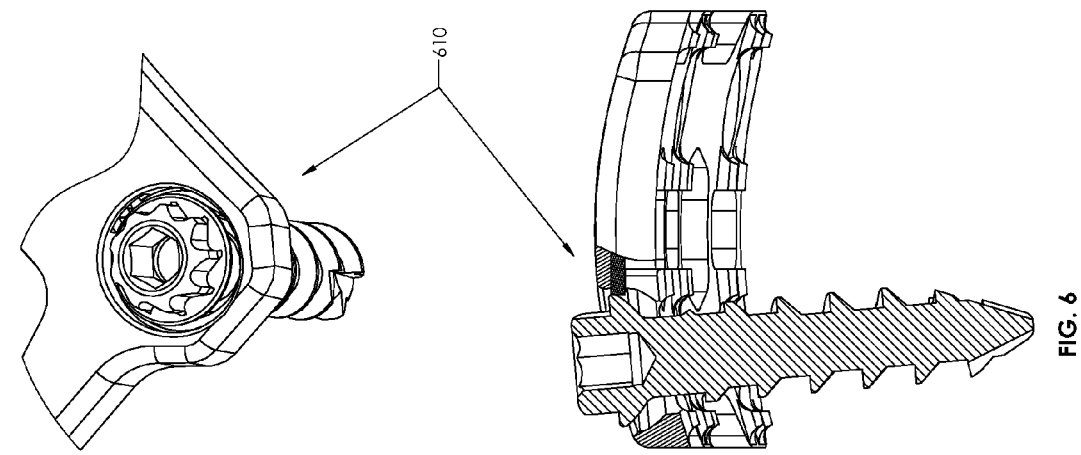
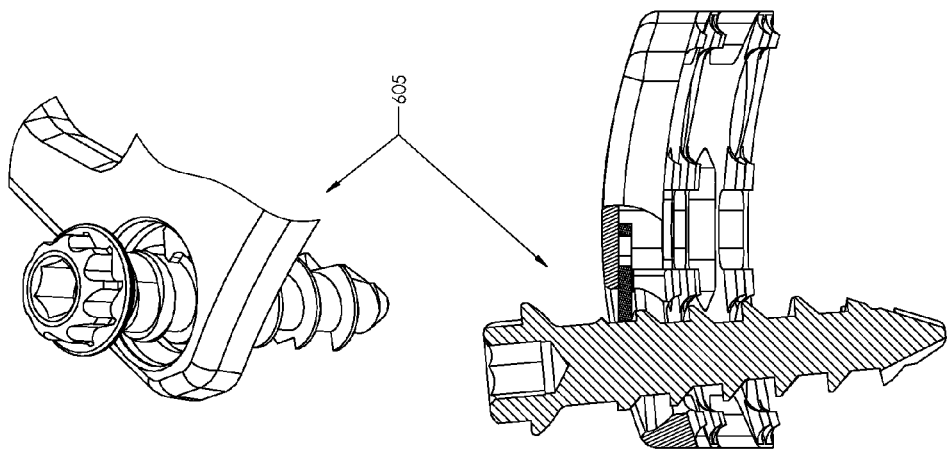
FIG. 6

SPINAL PLATE AND LOCKING SCREW DEVICES, METHODS, AND SYSTEMS

BACKGROUND

Spinal fixation devices can be used to provide, for example, immobilization and stabilization of spinal segments in patients (e.g., humans, dogs, cats, and other animals). Fixation devices may be used to help fuse bone segments (e.g., vertebrae) in the treatment of instabilities or deformities of, for example, the cervical, thoracic, lumbar, and/or sacral spine. Such instabilities or deformities may include, for example, degenerative disc disease (DDD); spondylolisthesis; trauma (i.e., fracture or dislocation); spinal stenosis; curvatures (i.e., scoliosis, kyphosis, and/or lordosis); tumor; pseudoarthrosis; and failed previous fusions.

However, there are risks associated with such fixation devices. Such risks include, for example, device component fracture, loss of fixation when the device/tissue bond is weakened or lost, non-union, fracture of the vertebra, neurological injury, and vascular or visceral injury. For example, internal fixation appliances are load sharing devices used to obtain bone alignment until normal healing occurs. Thus, implants are subjected to loads such as repetitive loads that occur when fixation systems are subjected to loading associated with, for example, normal patient movements (e.g., walking and bending), delayed union, or non-union situations. These loads can cause screws, which couple a fixation plate to bone, to loosen. The screws may loosen by, for example, backing out. This "backing out" may occur due to unwanted screw rotation (e.g., when the screw rotates and "unscrews" from the bone) and/or unwanted screw axial movement that is directed away from the bone. The axial movement may or may not be caused by the unwanted screw rotation. When a screw or screws back out and away from the plate and bone, the plate may become unstable and lead to complications for the patient. The degree or success of union, loads produced by weight bearing, and activity levels will, among other conditions, dictate the longevity of the implant. Robust fixation systems are needed to lessen risks associated with fixation and to promote better outcomes for patients.

BRIEF DESCRIPTION OF THE DRAWINGS

Features and advantages of embodiments of the present invention will become apparent from the appended claims, the following detailed description of one or more example embodiments, and the corresponding figures, in which:

FIGS. 2*a-c* include different perspectives of a resilient member in an embodiment of the invention.

FIGS. 3*a-e* include different perspectives of a screw in an embodiment of the invention.

FIGS. 4*a-e* include different perspectives of a plate in an embodiment of the invention.

FIG. 6 includes various implant states for an embodiment of the invention.

DETAILED DESCRIPTION

In the following description, numerous specific details are set forth. However, it is understood that embodiments of the invention may be practiced without these specific details. Well-known structures and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, structures, or characteristics. Further, some embodiments may have some, all, or none of the features described for other embodiments. Also, as used herein "first", "second", "third" and the like describe a common object and indicate that different instances of like objects are being referred to. Such adjectives are not intended to imply the objects so described must be in a given sequence, either temporally, spatially, in ranking, or in any other manner. Also, the terms "coupled" and "connected," along with their derivatives, may be used. In particular embodiments, "connected" may be used to indicate that two or more elements are in direct physical contact with each other and "coupled" may mean that two or more elements co-operate or interact with each other, but they may or may not be in direct physical contact.

An embodiment of the invention provides for a system, such as a cervical plate fusion system, that has mechanisms for preventing bone anchors (e.g., screws, pins, and the like) from backing out of the plate. The system prevents both counter-rotation of the screw and axial backing out of the screw. Other embodiments are described herein.

Figure 1C:
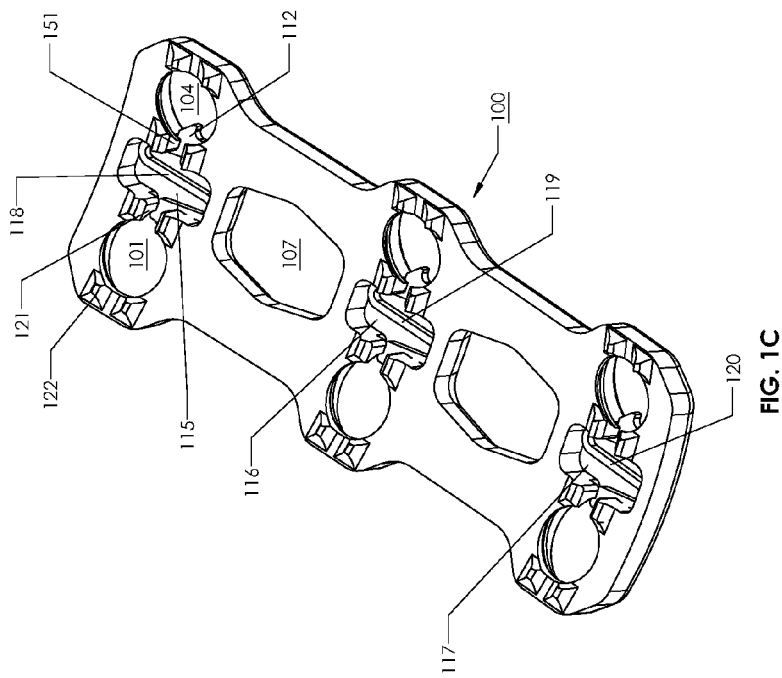
FIGS. 1*a-c* include different perspectives of a plate in an embodiment of the invention.
Figure 1A:
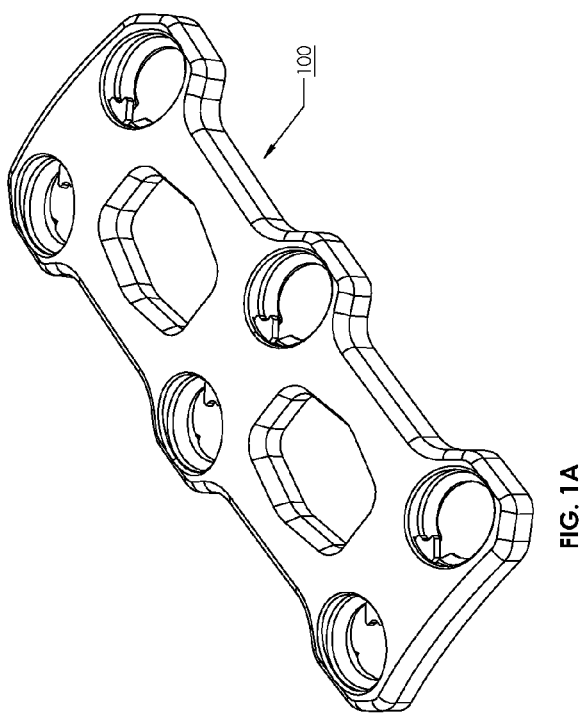
Figure 1B:
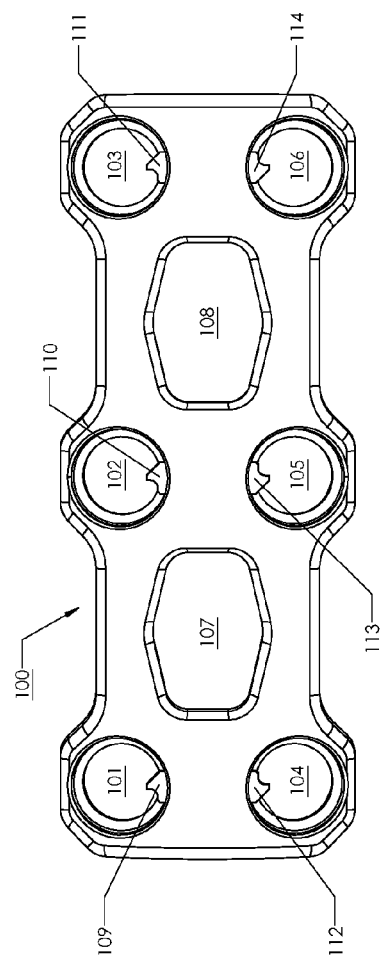

FIGS. 1*a-c* include plate 100. Plate 100 may be used for fusion of cervical vertebrae but may also be used for fusion of other vertebrae (e.g., thoracic, lumbar) or for fixation of other tissues (e.g., adjacent bone sections of a femur or other bone or tissue) and the like.

Plate 100 includes apertures 101, 102, 103, 104, 105, 106. These apertures or holes may have continuous perimeters but may also include discontinuous perimeters that do not form a complete circle, oval, rectangle and the like. The apertures (e.g., holes) need not be circular, symmetrical, or have any one particular perimeter, even though apertures 101, 102, 103, 104, 105, 106 each include a generally continuous circular perimeter. The three pairs of holes (101 and 104, 102 and 105, 103 and 106) of plate 100 are for a two level fusion system where two vertebral discs are to be fused. For example, only holes 101, 102, 104, 105 would be needed for a one level fusion. (FIG. 4*a* is configured for a one level fusion system.) A fourth pair of holes may be needed for a three level fusion.

Plate 100 includes cavities 115, 116, 117. Cavity 115 is described in greater detail herein but functions largely in the same manner as cavities 116, 117. Cavity 115 connects to holes 101, 104.

As seen in FIGS. 1*a-c*, single-piece monolithic resilient members 118, 119, 120 are respectively included in cavities 115, 116, 117. Resilient member 118 is described in greater detail herein but functions largely in the same manner as resilient members 119, 120. In FIGS. 2*a-c*, member 218 includes arms 252, 258 respectively connected to ends having fins 209, 212. During manufacturing member 218 may be stamped out in the "S" pattern shown in FIGS. 2*a-b*. The stamped member may be stamped out as a single monolithic element with no weldings or fixtures used to assemble member 218.

In FIGS. 3*a-e*, screw 340 includes lip 341, which is coupled to an angled or beveled shoulder 344, and a toothed wheel 365 having teeth such as tooth 348 and tooth 349.

Figure 5:
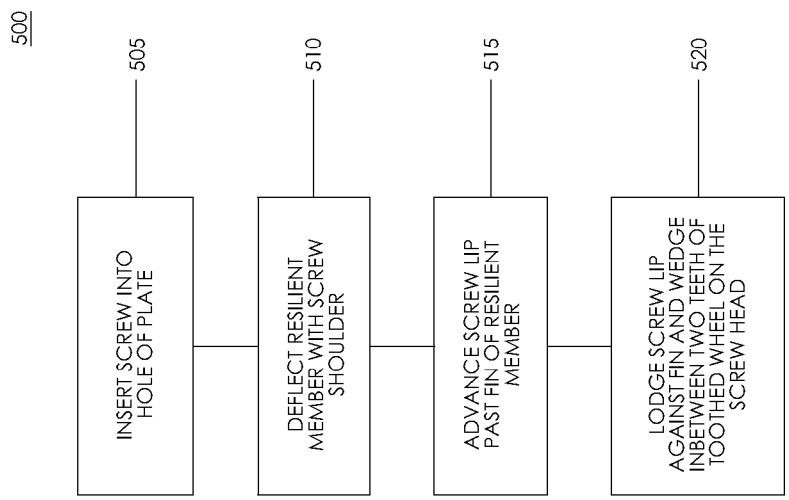
FIG. 5 includes a schematic flow chart for a method in an embodiment of the invention.

FIG. 5 includes method 500, which addresses various embodiments of the invention. For example, in block 505 a user inserts screw 340 into hole 101 (which may be adjacent projection 122 in an embodiment) of plate 100. Cavity 115 includes channels 121, 151 that respectively include first and second portions of resilient member 118. Fins 109, 112 respectively project into holes 101, 104 (and fins 110, 111, 113, 114 respectively project into holes 102, 103, 105, 106). Thus, at least a portion of fins 109, 112 project into holes 101, 104.

In an embodiment, resilient member 118 is seperably coupled to plate 100. For example, during assembly (e.g., at a manufacturing plant, in an operating room, in a medical office, etc.) member 118 may be compressed and then inserted into cavity 115. In an embodiment, member 118 is retained within cavity 115 based on a resistance fit where member 118 does not require use of a weld, screw, clamp, or the like to hold member 118 within cavity 115. Consequently, member 118 has advantages related to ease of manufacturing and also related to ease of assembly into plate 100. In an embodiment, cavity 118 remains generally open and un-enclosed upon final implantation of the system into the patient. Also, placing member 118 within (partially or fully) cavity 115 helps reduce the overall profile of the plate system, thus providing a less intrusive system for the patient.

As seen in FIG. 2, fin 209 has an angled leading edge 223 and a curved trailing edge 224, leading edge 223 being non-orthogonally connected to arm 252. Regarding the screw that interfaces member 218, FIG. 3 shows how tooth 348 has angled leading edge 342 and curved trailing edge 343, leading edge 342 being non-orthogonal to tangent 354 that intersects toothed wheel 365 at the same point as angled leading edge 342. Fin 209 is sized to be received between teeth 348, 349 of toothed wheel 365.

In FIG. 6, state 605 depicts an embodiment of the invention with a screw inserted into a hole.

Returning to FIG. 5, in block 510 shoulder 344 of screw 340 deflects member 118. Specifically, when screw 340 is in a partially implanted position and is being inserted into hole 101 beveled shoulder 344 is actively deflecting fin 109 medially towards cavity 115. In FIG. 6, state 610 depicts an embodiment of the invention with a fin deflected by a shoulder.

In block 515, the user advances screw 340 into a fully implanted position such that screw 340 is prevented from backing out of hole 101 by fin 109. In block 520 fin 109 has snapped back laterally (after having been deflected medially in block 510) into hole 101 to now intercept lip 341 if and when screw 340 "backs out" or travels (or attempts to "back out" or travel) axially away from patient bone in which it is implanted. Also, while toothed wheel 365 is allowed to rotate in one direction (e.g., clockwise to tighten screw 340 into bone) toothed wheel 365 is prevented from counter-rotating (e.g., counter clockwise to loosen and "back out" from bone) because trailing edge 224 of fin 209 is lodged against trailing edge 343 of tooth 348. In FIG. 6, items 615, 620 depicts an embodiment of the invention with a fin "snapped back laterally."

FIG. 4 includes an embodiment of the invention where holes 401, 404 are bisected by horizontal axis 455, which is orthogonal to the midline of a patient in which the system is configured for implantation and long axis 456 of plate 400. Plate 400 also includes holes 402, 405 and another cavity (e.g., cavity 116). Holes 402, 405 are bisected by horizontal axis 457, which is orthogonal to long axis 456. Plate 400 includes viewing aperture 407, which allows patient tissue to be viewed by a user upon implantation of the system into a patient, located along long axis 456 and fully or partially between axes 455, 457. Bone tissue may be inserted through aperture 407 to facilitate fusion. As seen in FIG. 1, member 118 does not project into aperture 107 or aperture 108. Also, cavity 115 does not connect to aperture 107. Returning to FIG. 4, 401, 402, 404, 405 are all included in a single level of the plate, the single level corresponding to a single level of fusion within the patient.

In an embodiment, member 118 includes nitinol. However, in other embodiments member 118 includes other materials such as stainless steel and the like. In an embodiment, member 118 includes an "S" shaped profile but may include other shaped profiles (e.g., ovular, circular) in other embodiments. In an embodiment, arm 252 couples to arm 258 via body 253. When resilient member 218 is fully compressed for insertion into cavity 115 arms 252, 258 may both be compressed against body 253.

In an embodiment, screw 340 includes tooth 348, which has a height 359 sized so when the screw is fully implanted (e.g., with shoulder 344 directly against bone) fin 109 will always be in contact with a portion of tooth 348. In other words, in an embodiment fin 109 projects medially out from "T" channel 421 (FIG. 4) (similarly another tooth projects medially out from "T" channel 451 in some embodiments). If height 359 is too small, fin 109 could spring or project over tooth 348 and possibly loose contact with tooth 348. In such a case screw 340 may begin working loose when not in constant contact with a tooth include on the toothed wheel because there would be no immediate barrier to axial "back out" movement and/or loosening counter-rotation. However, such a scenario may be mitigated or eliminated by properly sizing height 359 so when the screw is fully implanted fin 109 will always be in contact with a portion of tooth 348.

In an embodiment, horizontal axis 461 intercepts the first and second fins (not shown) of a single level. Axis 461 does not intercept lateral wall portion 462 of hole 401 but does intercept medial wall 463 of hole 401. Thus curvature of the plate provides for proper lordosis. Also, having horizontal axis 461 intercept the first and second fins of a single level provides benefits in manufacturing as plates with one, two, or three fusion levels are of similar design but for using one, two, or three resilient members. Thus, the design of the system allows for scaling between various embodiments that correspond to varying fusion levels.

In various embodiments, resilient member 218 includes dimension 230 of generally 0.3, 0.4, 0.5, 0.6, 0.7, or 0.8 mm. Member 218 includes dimension 233 of generally 1.1, 1.2, 1.3, 1.4, 1.5, 1.6, 1.7, or 1.8 mm. Member 218 includes dimension 225 of generally 6.5, 6.6, 6.7, 6.8, 6.9, 7.0, 7.1, 7.2, 7.3, or 7.4 mm. Member 218 includes dimension 232 of generally 0.3, 0.4, 0.5, 0.6, or 0.7 mm. Member 218 includes dimension 234 of generally 1.4, 1.5, 1.6, 1.7, 1.8, 1.9, or 2.0 mm. Member 218 includes dimension 229 of generally 0.1, 0.2, 0.3, 0.4, or 0.5 mm. Member 218 includes dimension 228 of generally 0.3, 0.4, 0.5, 0.6, 0.7, 0.8, or 0.9 mm. Member 218 includes dimension 226 of generally 0.4, 0.5, 0.6, 0.7, 0.8, 0.9, or 1.0 mm. Member 218 includes dimension 227 of generally 0.1, 0.2, 0.3, 0.4, 0.5, or 0.6 mm. However, other sizings and dimensions (such as dimension 231) are within the scope of the embodiments and may be dictated according to load requirements (e.g., amount of load, duration of load bearing, etc.).

In various embodiments screw 340 includes height 359 of generally 1.2, 1.3, 1.4, 1.5, 1.6, 1.7, or 1.8 mm. Screw 340 includes dimension 360 of generally 2.8, 2.9, 3.0, 3.1, 3.2, or 3.3 mm. Screw 340 includes dimension 345 of generally 0.1, 0.2, 0.3, 0.4, 0.5, or 0.6 mm. Screw 340 includes dimension 346 of generally 60, 65, 70, 75, 80, or 85 degrees. Screw 340 includes dimension 347 of generally 0.1, 0.2, 0.3, or 0.4 mm.

In various embodiments plate 400 includes dimension 450 of generally 0.4, 0.5, 0.6, 0.7, 0.8, 0.9, or 1.0 mm.

In one embodiment, a medial force directed to fin 109 translates to a lateral force directed to fin 112. Thus, a counter-rotation of a screw in hole 101 may produce a medial force against fin 109, which may then translate along monolithic member 118 and into a lateral force along fin 112, which may prevent a screw in hole 104 from counter-rotating or even moving axially and backing out.

In various embodiments, a plate may forego use of a cavity (that corresponds to a resilient member) and may instead couple the resilient member to an outer surface of the plate. The resilient member may also be integral or monolithic with the plate. Also, fins may include various geometries and may include, for example, orthogonal dimensions such that the fin has straight edges that fit at right angles to an arm of resilient member. The fin may be rectangular, square, and the like. The same may be the case for teeth on the screw such that the teeth may have straight edges that fit at right angles to the toothed wheel. Resilient members do not necessarily need to project into two holes. Instead, for example, a resilient member may be dedicated to a single hole and resisting backing out of the single screw that corresponds to the single hole. Also, a single resilient member may be applied to three or more holes. In such a case, the broader resilient member may be included in or over a cavity that, for example, winds around the plate with channels connecting to three or more holes. Also, embodiments do not necessarily require that the screw include a "highly" toothed wheel but may also include a screw with a few (e.g., one or two) simple projections that serve as teeth to accomplish the goal of preventing unwanted rotation. Also, while "rotation" and "counter rotation" have been used herein those terms should not be assumed to be associated with, for example, any particular direction such as "clockwise" for "rotation" or "counter clockwise" for "counter rotation." Also, screws may include lips that are not necessarily limited to flanges and the like. Lips may include floors or basic impediments to, for example, vertical or axial movement away from bone.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. An orthopedic fusion system comprising:
    a plate that includes first and second holes and a first cavity connecting the first and second holes;
    a single-piece monolithic resilient member included in the first cavity, the resilient member including a first arm connected to a first end having a first fin and a second arm connected to a second end having a second fin;
    a screw including a lip, which is coupled to a beveled shoulder, and a toothed wheel having first and second teeth;
    wherein (a) the resilient member is seperably coupled to the plate and within the first cavity; (b) the first cavity includes first and second channels that respectively include first and second portions of the resilient member; (c) the first and second fins respectively project into the first and second holes; (d) the first fin has a first angled leading edge and a first curved trailing edge, the first angled leading edge of the first fin being non-orthogonally connected to the first arm; (e) the first tooth has a first angled leading edge and a first curved trailing edge, the first angled leading edge of the first tooth being non-orthogonal to a tangent intersecting the toothed wheel at a same point the first angled leading edge of the first tooth intersects the toothed wheel; and (f) the first fin is sized to be received between the first and second teeth of the toothed wheel;
    wherein the system is configured such that (g) in a partially implanted position the screw is inserted into the first hole and the beveled shoulder is actively deflecting the first fin medially towards the first cavity; and (h) in a fully implanted position (1) the screw is inserted into the first hole such that the screw is prevented from backing out of the first hole by the first fin that has snapped back into the first hole to intercept the lip when the screws travels axially away from patient bone in which it is implanted and (2) the toothed wheel is allowed to rotate but is prevented from counter-rotating because the first curved trailing edge of the first fin is lodged against the first trailing edge of the first tooth.

2. The system of claim 1, wherein the resilient member includes nitinol.

3. The system of claim 1, wherein the first and second holes are bisected by a first horizontal axis, which is orthogonal to the (a) midline of a patient in which the system is configured for implantation and (b) a long axis of the plate.

4. The system of claim 3, wherein:
    the plate includes third and fourth holes and a second cavity connecting the third and fourth holes, the third and fourth holes being bisected by a second horizontal axis that is orthogonal to the midline of the patient and the long axis of the plate;
    a first viewing aperture, which allows patient tissue to be viewed upon implantation of the system, located along the long axis of the plate and between the first and second horizontal axes;
    the resilient member does not project into the first viewing aperture;
    the first cavity does not connect to the first view aperture; and
    the first, second, third, and fourth holes are all included in a single level of the plate, the single level corresponding to a level of fusion within the patient.

5. The system of claim 3, wherein:
    the plate includes third and fourth holes and a second cavity connecting the third and fourth holes, the third and fourth holes being bisected by a second horizontal axis that is orthogonal to the midline of the patient and the long axis of the plate;
    a first viewing aperture, which allows patient tissue to be viewed upon implantation of the system, located along the long axis of the plate and between the first and second horizontal axes;
    the resilient member does not project below any portion of the first viewing aperture;
    the first cavity does not project below any portion of the first viewing aperture;
    the first cavity does not connect to the first view aperture;
    the first, second, third, and fourth holes each include a continuous enclosed perimeter separate and apart from a perimeter of the viewing aperture; and
    the first, second, third, and fourth holes are all included in a single level of the plate, the single level corresponding to a level of fusion within the patient.

6. The system of claim 1, wherein the resilient member is retained within the first cavity based on a resistance fit and without use of a weld, screw, or clamp.

7. The system of claim 1, wherein the resilient member includes an "S" shaped profile.

8. The system of claim 1, wherein the first tooth includes a first height, as measured from the lip to the top of the first tooth, which is sized so when the screw is fully implanted the first fin will always be in contact with a portion of the first tooth.

9. The system of claim 1, wherein the first arm connects to the second arm via a first body so when the resilient member is fully compressed for insertion into the first cavity the first and second arms may both be compressed against the first body.

10. The system of claim 1, wherein the first cavity remains open and un-enclosed upon final implantation of the system into the patient.

11. The system of claim 1, wherein a horizontal axis (a) intercepts the first and second fins, (b) does not intercept a lateral wall of the first hole, and (c) intercepts a medial wall of the first hole.

12. The system of claim 1, wherein the resilient member is configured so a medial force directed to the first fin translates to a lateral force directed to the second fin.

13. An orthopedic system comprising:
a plate that includes first and second holes;
a resilient member including a first arm and a second arm;
a bone anchor including a lip, which is coupled to a shoulder, and first and second teeth;
wherein (a) the first and second arms respectively project to the first and second holes; (b) the first arm has a first leading edge and a first trailing edge; (c) the first tooth has a first leading edge and a first trailing edge; and (d) the first arm is sized to be received between the first and second teeth;
wherein the system is configured such that (e) in a partially implanted position the bone anchor is inserted into the first hole and the shoulder is actively deflecting the first arm; and (f) in a fully implanted position (1) the bone anchor is inserted into the first hole such that the bone anchor is prevented from backing out of the first hole by the first arm that has snapped back to the first hole to intercept the lip when the bone anchor travels axially away from patient bone in which it is implanted, and (2) the bone anchor is allowed to rotate but is prevented from counter-rotating because the first trailing edge of the first arm is lodged against the first trailing edge of the first tooth;
wherein a horizontal axis (a) intercepts the first and second arms, (b) does not intercept a lateral wall of the first hole, and (c) intercepts a medial wall of the first hole.

14. The system of claim 13, wherein the first and second holes are bisected by a first horizontal axis, which is orthogonal to the (a) midline of a patient in which the system is configured for implantation and (b) a long axis of the plate.

15. The system of claim 13, wherein the first tooth includes a first height, as measured from the lip to the top of the first tooth, which is sized so when the bone anchor is fully implanted the first arm will always be in contact with a portion of the first tooth.

16. The system of claim 15, wherein the resilient member is configured so a medial force directed to the first arm translates to a lateral force directed to the second arm.

17. An orthopedic system comprising:
a plate that includes first and second holes and a first cavity connecting the first and second holes;
a single-piece monolithic resilient member configured to be included in the first cavity, the resilient member including a first arm connected to a first end having a first fin and a second arm connected to a second end having a second fin;
wherein (a) the resilient member is configured to be seperably coupled to the plate and within the first cavity; (b) the first cavity includes first and second channels that respectively include first and second portions of the resilient member; (c) the first and second fins respectively project into the first and second holes; (d) the first fin has a first angled leading edge and a first curved trailing edge, the first angled leading edge of the first fin being non-orthogonally connected to the first arm;
wherein the system is configured such that (e) when a bone anchor, in a partially implanted position, is inserted into the first hole a beveled shoulder included in the bone anchor actively deflects the first fin medially towards the first cavity; and (f) when the bone anchor, in a fully implanted position, is inserted into the first hole (1) the bone anchor is prevented from backing out of the first hole by the first fin that has snapped back into the first hole to intercept a lip, included in the bone anchor, when the bone anchor travels axially away from patient bone in which it is implanted, and (2) the bone anchor is allowed to rotate but is prevented from counter-rotating because the first curved trailing edge of the first fin is lodged against a first trailing edge of a first tooth included in the bone anchor.

18. The system of claim 17, wherein the first and second holes are bisected by a first horizontal axis, which is orthogonal to the (a) midline of a patient in which the system is configured for implantation and (b) a long axis of the plate.

19. The system of claim 17 comprising the bone anchor, wherein the first tooth includes a first height, as measured from the lip to the top of the first tooth, which is sized so when the bone anchor is fully implanted the first fin will always be in contact with a portion of the first tooth.

20. The system of claim 19, wherein a horizontal axis bisects the first and second fins and the horizontal axis does not intercept a lateral wall of the first hole but does intercept a medial wall of the first hole.

* * * * *

UNITED STATES PATENT AND TRADEMARK OFFICE
CERTIFICATE OF CORRECTION

PATENT NO. : 8,784,459 B2  
APPLICATION NO. : 13/351340  
DATED : July 22, 2014  
INVENTOR(S) : Josh Kaufmann et al.

Page 1 of 1

It is certified that error appears in the above-identified patent and that said Letters Patent is hereby corrected as shown below:

On the title page item 12

United States Patent
  Kaufman et al."

should be

--United States Patent
  Kaufmann et al.-- and item 75

"Inventors: Josh Kaufman, Austin, TX (US); Scott Bryant, Austin, TX (US); Greg Calbert, Lakeway, TX (US); John Stokes, Austin, TX (US); Matthew Geck, Austin, TX (US); Landon Gilkey, Austin, TX (US)"

should be

--Inventors: Josh Kaufmann, Austin, TX (US); Scott Bryant, Austin, TX (US); Greg Calbert, Lakeway, TX (US); John Stokes, Austin, TX (US); Matthew Geck, Austin, TX (US); Landon Gilkey, Austin, TX (US)--

Signed and Sealed this
Eighth Day of March, 2016

Michelle K. Lee
*Director of the United States Patent and Trademark Office*